United States Patent [19]

Vernice et al.

[11] Patent Number: 5,405,622
[45] Date of Patent: Apr. 11, 1995

[54] GAMMA RADIATION RESISTANT LUBRICATING GEL

[76] Inventors: Joseph Vernice, 80 Parkview Dr. W., Shirley, N.Y. 11967; Alfred R. Globus, 26-53 210th St., Bayside, N.Y. 11360

[21] Appl. No.: 171,631

[22] Filed: Dec. 22, 1993

[51] Int. Cl.$^6$ .................. A01N 59/02; A61L 2/00
[52] U.S. Cl. .................. 424/711; 514/772.1; 422/22
[58] Field of Search .................. 424/711; 422/22; 514/772.1

[56] References Cited

U.S. PATENT DOCUMENTS

| | | | |
|---|---|---|---|
| 4,427,631 | 1/1984 | Bunting et al. | 422/22 |
| 4,781,923 | 11/1988 | Pellico | 424/130 |
| 4,826,828 | 5/1989 | Wilmott et al. | 514/63 |
| 4,837,019 | 6/1989 | Georgalas et al. | 424/101 |
| 4,847,267 | 7/1989 | Deckner et al. | 424/711 |
| 4,942,038 | 7/1990 | Wallach | 424/450 |
| 5,250,289 | 10/1993 | Boothroyd et al. | 424/59 |

FOREIGN PATENT DOCUMENTS

| | | | |
|---|---|---|---|
| 0055702 | 7/1982 | European Pat. Off. | 424/711 |
| 55-129211 | 10/1980 | Japan | 404/211 |

*Primary Examiner*—Thurman K. Page
*Assistant Examiner*—Peter F. Kulkosky
*Attorney, Agent, or Firm*—Evelyn M. Sommer

[57] ABSTRACT

A gamma radiation stable gel consisting mainly of the complex of polyglyceryl methacrylate and at least one alkali metal or ammonium sulfite, bisulfite or metabisulfite.

This gel is sterilizeable, bland water soluble, clear and colorless, washable, non-staining lubricating jelly. It is harmless to skin, delicate tissues and mucous membranes. It will not affect surgical instruments or rubber appliances. The gel of the invention may also be used as a drug delivery vehicle.

A method of preparing the gel is also disclosed.

22 Claims, No Drawings

GAMMA RADIATION RESISTANT LUBRICATING GEL

This invention relates to a gamma radiation stable gel. More particularly, this invention is directed to a gamma radiation resistant gel characterized by a formulation consisting mainly of polyglyceryl methacrylate and small amounts of sodium, potassium and/or ammonium sulfite, bisulfite or metabisulfite, the balance of the complex being water, both free and complexed as a clathrate within the polyglyceryl methacrylate moiety (LUBRAJEL RR).

In accordance with this invention, it has now been found that complexes of polyglyceryl methacrylate (LUBRAJEL$^R$) with sulfite, bisulfite or metabisulfite are stable to cobalt $^{60}$ ($^{60}$Co) gamma radiation to the extent of 4.5 megarads. The complexes of the invention are intended for use, for example, with medical devices whenever a sterile water soluble lubricant is required. Such devices would include thermometers, catheters, specula, stomach tubes, sounds, cystoscopes, proctoscopes, Instruments used in urological, rectal, and vaginal examinations, and for endotracheal intubations. The complexes of the invention can also be used as a lubricant on examination gloves in rectal or gynecological examinations.

The gels of the invention are bland water soluble, readily washable, non-staining lubricating gels. They are harmless to skin, delicate tissues and mucous membranes. They will not affect surgical instruments or rubber appliances.

The gel of the invention may also be used as a drug delivery vehicle.

Presently, methods available for sterilization include the following:

Moist Heat—high pressure steam sterilization—The use of high pressure steam (autoclave) is the most common method of sterilization in use today. Disadvantages of autoclaving include denaturation of proteins and inactivation of many biologically active substances, as for example, vitamins.

Gaseous sterilization—three main chemicals have been conventionally used—ethylene oxide, formaldehyde and beta-propiolactone.

Ethylene oxide—disadvantages are untoward effects on certain chemicals particularly vitamins and amino acids. Undesired residuals may also be a problem.

Formaldehyde—due to toxicity it is not being used at present.

Beta-propiolactone—a product of ketone and formaldehyde is also not being used due to attendant toxicity.

Radiation—Three types of radiation have assumed importance in the sterilization of biological materials; ultra-violet light, gamma and x-ray radiation.

Ultra-violet light—disadvantages associated with its use are that the required time of exposure is usually long, rays do not pass through glass, and the short penetration of such rays.

X-Rays—generally not used

Gamma radiation—Cobalt $^{60}$ has been the most commonly used gamma emitter in sterilization. A dosage level of 2.0 to 2.5 megarads is sufficient for medical applications. In practice, gamma radiation sterilization has been used to sterilize dressings, syringes, catheters, implants and other medical items. It is used extensively as a means for preserving food. The safety, (lack of any known toxicity), associated with gamma radiation supports the use of this means of sterilization. It has not however, heretofore been used in connection with a gel formulation, particularly because such formulations are not stable to such treatment and undergo disintegration or separation into different phases.

The application or use of the gels of the invention would often occur in instances where pathology (damaged or altered tissues) exists and therefore a non-irritating, non-sensitizing product is preferable. The exposure time of LUBRAJEL to gamma radiation is approximately two times the sterilizing dose. Classically, applicable techniques have been autoclaving and ethylene oxide sterilization of which autoclaving is often not desirable because of material limitations and ethylene oxide results in the formation of undesired residuals such as ethylene glycol, epichlorohydrin and residual ethylene oxide.

The invention herein lies in the provision of a gamma radiation stable gel characterized by a formulation containing between about 40 and about 92-99.2% by weight (LUBRAJEL$^R$)[1]. The polyglyceryl methacrylate component is in the form of a white transparent gel containing 50 to about 75% by weight solids which may or may not contain incidental ingredients such as propylene glycol. LUBRAJEL is a clathrate formed by the reaction of glycerin and methylmethacrylate. The formulation of this invention also contains between about 0.01 and about 2.0% by weight and preferably not more than 0.5% by weight of at least one alkali metal sulfite, bisulfite or metabisulfite preferably sodium or potassium. The balance of the complex is water, both free and complexed as a clathrate within the polyglyceryl methacrylate moiety.

[1] LUBRAJEL is a registered trademark of United-Guardian, Inc.

The product of the invention (LUBRAJEL RR) is a complex of polyglyceryl methacrylate (LUBRAJEL) with a sulfite, bisulfite or metabisulfite anion. The complex with the sulfite, bisulfite or metabisulfite anions is responsible for the stabilization against loss in viscosity and change in pH subsequent to irradiation with $^{60}$Co. It is theorized that the polyglyceryl methacrylate anion complex functions to quench any free radicals that are produced during the irradiation process. The mechanism, although not known, cannot be a simple free radical quenching, since the addition of sulfite, bisulfite or metabisulfite to other gel lubricants presently on the market does not stabilize against degradation.

Complexation of the components of LUBRAJEL RR occurs only under specific conditions. The complexes or clathrate form at pH's between about 4.5 and about 6.0 and are most stable between about 4.8 and about 6.0. The complexing reaction takes place at ambient temperatures and normal pressures (20°–40° C./750–770 mm Hg). Since the heat of formation of the complex is negative, the equilibrium favors its formation. The complexation takes place in about 24–48 hours.

The stability of the clathrate is determined by the viscosity of the material. Upon collapse of the clathrate, the viscosity is dramatically reduced. The clathrate is also disrupted by ionic materials, polar solvents and other materials that may have a stronger affinity for water than the complex itself.

Typically, synthesis of the complex involves preparation of a concentrated aqueous solution of the sodium, potassium or ammonium salts of sulfite, bisulfite or metabisulfite or any combination thereof. The resultant solution is labeled as (I).

The solution is assayed for reducing efficiency by generally accepted methods such as those found in the Food Chemical Codex or the United States Pharmacopeia. This usually consists of reacting the sulfite with an excess of iodine and performing a titration of the excess iodine.

The complexes of the invention are prepared as follows: In a suitable container charged with 40-99% by weight polyglyceryl methacrylate (LUBRAJEL), between 0.01 and 0.5 and preferably 0.5% by weight of (I) in the form of its solution are added and the components mixed together thoroughly. The complexation or clathrate formation takes place at a pH of between about 4.5 and about 6.0, preferably about 4.8 to about 5.5 at ambient temperature (20° to 400° C.) and normal pressure (750-770 mm Hg) in 24-48 hours.

The pH of the resultant gel is adjusted with a 10% solution of sodium hydroxide to between about 4.5 and about 6.5 and preferably from about 4.8 and about 5.5.

Nine months of stability data has been accumulated for the gel LUBRAJEL RR. The parameters monitored were pH, color, clarity and viscosity. The products were monitored in both the non-irradiated and irradiated states. The irradiation was carried out using ISOMEDIX Corporation facilities in Whippany, N.J. Radiation dosage in this instance was limited to 3.5 megarads.

Stability was determined at ambient temperature as well as at stressed temperatures. The data obtained indicates adequate pH and viscosity retention for establishment of a 24 month shelf life.

| PHYSICAL AND CHEMICAL PROPERTIES OF LUBRAJEL RR | |
| --- | --- |
| PARAMETER | RANGE |
| Appearance | clear, colorless |
| Viscosity | not less than 10,000 cps (22° C., Model DVII, sp#7, 50 rpm) |
| pH | 4.0-6.0 |
| Refractive Index | 1.381 |
| Stabilizer | 0.05-0.1% |
| Water Solubility | complete in all proportions |

LUBRAJEL RR is intended for use:
(1) with medical devices whenever a sterile, water soluble lubricant is required. Such devices would include thermometers, catheters, specula, stomach and nasal tubes, cystoscopes, sounds, proctoscopes, instruments used in urological, rectal and vaginal examinations, and for endotracheal intubations.
(2) the invention could be used as a lubricant on examination gloves in rectal or gynecological examinations.
(3) as a drug delivery vehicle.

The general impermeability of the skin to both hydrophobic and hydrophilic substances poses both disadvantages and advantages for topical administration of drugs to achieve local and systemic effects (peak rates are not achieved for 12-24 hours), however in some instances topical administration can avoid the rapid gastric absorption and rapid metabolism associated with oral administration. Topical administration also spreads out the active level of drug over a longer period of time. Topical administration has good patient compliance. In the case of LUBRAJEL RR, application to the mucous membranes by instillation of drug in LUBRAJEL RR would allow for a slowed absorption of drug (faster than if applied to the skin) and continued presence of drug over a period of time. An example of projected use would be the instillation of LUBRAJEL RR and drug, (into the bladder via a catheter or syringe) in urinary bladder infections. LUBRAJEL RR can also be used to deliver a wide variety of drugs such as antimicrobials, tranquilizers, anesthetics, contraceptives, etc. by delivery into the vagina, rectum, ear, nose and even the mouth (as a coating rinse) as well as for wound healing, etc. applied directly or on a dressing onto the wound, ulcer, damaged exposed tissue etc.

The following examples are given in order to illustrate the invention but are not to be construed in limitation thereof.

1. A formulation containing 80% by weight polyglyceryl methacrylate (LUBRAJEL) and 0.5% by weight of a concentrated solution of sodium sulfite were admixed. The pH of the mixture was adjusted to 5.0. The balance of the complex is water, both free and complexed as a clathrate within the polyglyceryl methacrylate moiety. The complex was clear and colorless.

2. A formulation containing 90.0% by weight polyglyceryl methacrylate (LUBRAJEL) and 2.0% by weight of a concentrated solution of potassium bisulfite were admixed. The pH of the mixture was adjusted to 4.9. The balance of the complex is water, both free and complexed as a clathrate within the polyglyceryl methacrylate moiety.

3. A formulation containing between 88.0% by weight polyglyceryl methacrylate (LUBRAJEL), and 1.0% by weight of a concentrated solution of ammonium metabisulfite were admixed. The pH of the mixture was adjusted to 5.0. The balance of the complex is water, both free and complexed as a clathrate within the polyglyceryl methacrylate moiety.

4. A formulation containing between 98.0% by weight polyglyceryl methacrylate (LUBRAJEL) and 0.05% by weight of a concentrated solution of a mixture of sodium, potassium and ammonium sulfite were admixed. The pH of the mixture was adjusted to 5.2. The balance of the complex is water, both free and complexed as a clathrate within the polyglyceryl methacrylate moiety.

5. Pharmaceutical compositions are prepared by incorporating the complex as set forth in either examples 1, 2, 3, and 4 with different pharmaceutical agents. The complex functions as a permeability modifier.
a) To the complex (example 1), nitroglycerine, 5 mg/100 grams is added. The formulation is intended for use in 10 gram amounts for controlling angina patients.
b) To the complex (example 2), scopolamine, 10 mg/100 grams is added. The formulation will be used in 10 gram amounts for the prevention of motion sickness.
c) To the complex (example 3), clotrimazole is added to yield a final concentration of 1% (1 gram clotrimazole/100 grams). This composition is utilized to treat fungal infections of the vagina, skin and nails. The formulation is to be used in 10 gram amounts.
d) To the complex (example 4), miconazole is added to yield a final concentration of 2% (2 grams miconazole/100 grams). This composition is utilized to treat fungal infections of the vagina, skin and nails. The formulation will be used in 10 gram amounts.
e) To the complex (example 1), hydrocortisone is added to yield a final concentration of 1% (1 gram hydrocortisone/100 grams). This composition is utilized to treat inflammatory conditions of the skin such as dermatitis due to plants or sensitizing agents, insect bites, burns etc. as well as to relieve itching associated with insect bites, allergic conditions such as hives etc. The formulation is to be used in 10 gram amounts.

I claim:

1. A clear and colorless lubricating gel stable to $_{60}$Co gamma radiation comprising a complex of polyglyceryl methacrylate with at least one member selected from the group consisting of alkali metal or ammonium sulfite, bisulfite or metabisulfite salts said salts being present in an amount of at least 0.05% by weight, the balance of the composition being free and/or bound water.

2. A lubricating gel according to claim 1 wherein said polyglyceryl methacrylate is present in an amount of between 40 and 99.6% by weight, said alkali metal sulfite, bisulfite or metabisulfite is present in an amount of between 0.01 and 2.0% by weight.

3. A lubricating gel according to claim 1 wherein said salt is a sodium, potassium or ammonium salt.

4. A lubricating gel according to claim 1 wherein said salt is sodium metabisulfite.

5. A lubricating gel according to claim 1 wherein said polyglyceryl methacrylate is present in an amount of 99.0% by weight, said sodium, potassium or ammonium sulfite, bisulfite or metabisulfite is present in an amount of 0.05% by weight.

6. A lubricating gel according to claim 1 wherein water is present in said gel in both free form and complexed as a clathrate within said polyglyceryl methacrylate.

7. A lubricating gel according to claim 1 wherein said polyglyceryl methacrylate is present in an amount of about 98.0% by weight, said salt is present in an amount of from at least 0.05 to 2% by weight.

8. A method of preparing the lubricating gel of claim 1 which comprises intimately admixing polyglyceryl methacrylate with at least one member of the group consisting of alkali metal and ammonium salts of sulfite, bisulfite and metabisulfite, at a pH of between 4.5 and 6.0 and subjecting the resultant mixture to a temperature of 20° to 400° C. and a normal pressure.

9. A method according to claim 8, wherein said salt is a sodium, potassium or ammonium salt.

10. A method according to claim 9, wherein said salt is sodium metabisulfite.

11. A method according to claim 8 which comprises admixing 98–99.95% by weight of polyglyceryl methacrylate with 0.01 to 2.0% by weight of sodium metabisulfite.

12. A method according to claim 10 which comprises admixing 99.95% by weight of polyglyceryl methacrylate with 0.05% by weight of sodium metabisulfite.

13. A method according to claim 8 which comprises the further step of sterilizing said lubricating gel by subjecting the same to $_{60}$Co gamma radiation or to electron beam radiation.

14. A method according to claim 8 which comprises the further step of sterilizing said lubricating gel by subjecting the same to gamma radiation at a dosage not exceeding 3.5 megarads.

15. The sterile lubricating gel produced by the method of claim 13.

16. A therapeutic composition comprising a lubricating gel according to claim 1 having incorporated therein an effective amount of a therapeutic agent.

17. A therapeutic composition according to claim 16 wherein said therapeutic agent is nitroglycerine.

18. A therapeutic composition according to claim 16 wherein said therapeutic agent is scopolamine.

19. A therapeutic composition according to claim 16 wherein said therapeutic agent is clotrimazole.

20. A therapeutic composition according to claim 16 wherein said therapeutic agent is miconazole.

21. A therapeutic composition according to claim 16 wherein said therapeutic agent is hydrocortisone.

22. A method of topically administering a therapeutic agent which comprises topically applying the composition of claim 16 to a subject in need thereof.

* * * * *